United States Patent
Lignell et al.

(12) 
(10) Patent No.: US 6,410,602 B1
(45) Date of Patent: Jun. 25, 2002

(54) METHOD OF INCREASING THE PRODUCTION AND IMPROVING THE QUALITY OF SEMEN

(75) Inventors: Ake Lignell, Varmdo; John Inborr, Lidkoping; Curt Nicolin, Grodinge, all of (SE)

(73) Assignee: Astacarotene AB, Gustavsberg (SE)

( * ) Notice: Subject to any disclaimer, the term of this patent is extended or adjusted under 35 U.S.C. 154(b) by 0 days.

(21) Appl. No.: 09/555,514

(22) PCT Filed: Nov. 26, 1998

(86) PCT No.: PCT/SE98/02138

§ 371 (c)(1),
(2), (4) Date: Jun. 6, 2000

(87) PCT Pub. No.: WO99/29313

PCT Pub. Date: Jun. 17, 1999

(30) Foreign Application Priority Data

Dec. 9, 1997 (SE) ............................................. 9704590

(51) Int. Cl.⁷ ...................... A61P 15/08; A61K 31/122; A61K 31/05
(52) U.S. Cl. ........................................ 514/689; 514/576
(58) Field of Search .................................. 514/689, 725

(56) References Cited

FOREIGN PATENT DOCUMENTS

| | | | |
|---|---|---|---|
| GB | 2289406 | * | 11/1995 |
| SE | 9300901-7 A | | 9/1994 |
| WO | WO 9608977 A | | 3/1996 |
| WO | WO 9735491 A | | 10/1997 |

OTHER PUBLICATIONS

File WPI, Derwent accession No. 92–396782, Biochem Inst et al., "Medium for dilution cryopreservation of farm animals sperm contains sugar, complex salt of ethylene di: amin tetra: acetic acid, egg yolk, chlorophyll, glycerine and water"; & SU,A1,706608, 920123, DW9248.

STN International, File Caplus, CAPLUS accession No. 1990:52954, Paramonova, L. et al., "Interaction of carotenoids with the superoxide anion radical in relation to their stabilizing effect during cryoconservation of sperm", & Dokl. Vses. Akad. S–kh. Nauk im. V.I. Lenina (1989).

* cited by examiner

Primary Examiner—Edward J. Webman
Assistant Examiner—Helen Nguyen
(74) Attorney, Agent, or Firm—Bacon & Thomas

(57) ABSTRACT

A method of increasing the volume, the total sperm count and the reproductive performance of semen from human and animal males, is described. The method comprises administration of an effective dosage of a human or veterinary preparation containing at least one type of xanthoplylls, such as astaxanthin, to said males. Preferably, the astaxanthin exists in a form esterified with fatty acids, e.g. in the form of algal meal produced by culturing of the alga Haematococcus sp. Further, the use of at least one type of xanthophylls, such as astaxanthin, for the preparation of a human or veterinary preparation for increasing the volume, the total sperm count and the reproductive performance of semen from human and animal males, is disclosed.

6 Claims, No Drawings

METHOD OF INCREASING THE PRODUCTION AND IMPROVING THE QUALITY OF SEMEN

The present invention relates to a method of increasing the production and improving the quality of semen. More precisely, the invention relates to a method of increasing the volume, the total sperm count and the reproductive performance of semen from human and animal males. The method comprises administration of an effective dosage of a human or veterinary preparation containing at least one type of xanthophylls, such as astaxanthin, to the males. The invention also relates to the use of at least one type of xanthophylls, such as astaxanthin, for the preparation of a human or veterinary preparation for increasing the volume, the total sperm count and the reproductive performance of semen from human and animal males.

BACKGROUND

The quality of semen is of vital importance for the reproduction of both humans and animals. From an economical point of view the production of animals, by natural mating or artificial insemination, is of great importance in the food, poultry, livestock, animal breeding and domestic animal industry.

Our published International patent application WO 97/35491 relating to an agent for increasing the production of/in breeding and production mammals, discloses experiments wherein sows were given feed supplemented with astaxanthin during a period prior to parturition resulting in e.g. more piglets born alive. The mating boars did not receive any xanthophyll supplementation of their feed.

Astaxanthin, and other xanthophylls, are known to exhibit antioxidative properties, and hence possesses the ability to scavenge so-called free radicals. However, in biological tests astaxanthin has been shown to possess clearly the best antioxidative properties compared to other carotenoids (Miki W., 1991, Pure and Appl Chem 63 (1): 141–146).

DESCRIPTION OF THE INVENTION

The present invention is directed to a method of increasing the volume, the total sperm count and the reproductive performance of semen from human and animal males, comprising administration of an effective dosage of a human or veterinary preparation containing at least one type of xanthophylls to said males.

In a preferred embodiment the type of xanthophylls is astaxanthin. In a particularly preferred embodiment the astaxanthin exists in a form in which it is esterified with fatty acids. The last mentioned form of astaxanthin may be in the form of algal meal produced by culturing of the alga Haematococcus sp.

An effective dosage of the preparation contains e.g. 0.01 to 1 mg astaxanthin per kg body weight per day.

The invention is also directed to the use of at least one type of xanthophylls for the preparation of a human or veterinary preparation for increasing the volume, the total sperm count and the reproductive performance of semen from human and animal males.

Here again, in a preferred embodiment the type of xanthophylls is astaxanthin. In a particularly preferred embodiment the astaxanthin exists in a form in which it is esterified with fatty acids. The last mentioned form of astaxanthin may be in the form of algal meal produced by culturing of the alga Haematococcus sp.

For example, the amount astaxanthin in the preparation is 0.01 to 1 mg per body weight of the human or animal male.

In the present invention the human and veterinary preparations may comprise a mixture of different types of xanthophylls or different forms of the same xanthophyll, such as a mixture of synthetic astaxanthin and naturally produced astaxanthin.

The human and veterinary preparation of the invention may comprise additional ingredients which are pharmacologically acceptable inactive or active, such as flavoring agents, excipients, diluents, carriers, and the like, and it may be presented in a separate unit dose or in admixture with food or feed. Examples of separate unit doses are tablets, gelatin capsules and predetermined amounts of solutions, e.g., oil solutions, or emulsions, e.g., water-in-oil or oil-in-water emulsions. Examples of food in which the preparation of the invention may be incorporated is dairy products, such as yogurt, chocolate and cereals.

DESCRIPTION OF EXPERIMENTS

The preparation used in the experiments contained the xanthophyll astaxanthin which was produced via the alga Haematococcus sp. by AstaCarotene AB, Gustavsberg, Sweden, and the experimental animal model was boars.

Naturally produced astaxanthin can be obtained also from fungi and crustaceans, in addition to from alga. Astaxanthin from other sources, and other xanthophylls as well, are expected to be similarly useful for the purposes of the invention. An advantage of using astaxanthin from alga is, however, that the astaxanthin exists in a form esterified with fatty acids [Renström B. et al, 1981, Phytochem 20(11):2561–2564], which esterified astaxanthin thereby is more stable during handling and storage than free astaxanthin.

The experiment was conducted with boars for the purpose of establishing whether astaxanthin supplemented feed increases semen production and improves the reproductive performance even though the breeding sows do not receive such astaxanthin supplemented feed.

EXPERIMENTAL DESIGN

A total of 37 boars of several breeds used for AI (artificial insemination) were divided into two groups and randomly allocated to one of the two dietary treatments. The boars were fed a standard boar feed either with (3 g/day) or without added NOVASTA™ (the trade name of AstaCarothene AB for the algal meal preparation for animals) for 16 weeks. NOVASTA was fed as a top dressing (150 g NOVASTA, containing 1% astaxanthin, mixed with 850 g ground wheat) once daily.

Boars were collected as part of the normal routine of the boar shed. On average boars were collected once per week. Collection was by the gloved hand technique whilst boars were mounted on a dummy sow. Ejaculates were collected into warmed collection container after filtering to remove the gel fraction of the ejaculate. Each ejaculate was weighed to provide an estimate of the volume collected.

During the statistical analysis of the data the age of the boar at the time of collection was included as a covariate.

The semen produced by the boars was then used for mating sows of the commercial herd. There were 1036 mating carried out, 513 matings to NOVASTA supplemented boars and 523 matings to boars from the control group.

Results of the Experiments

| Semen production | | |
|---|---:|---:|
|  | Control | NOVASTA |
| Period 1 (0–6 weeks) | | |
| Volume (ml) | 151.250[a] | 211.400[b] |
| Sperm density (×10$^9$/ml) | 0.636[a] | 0.509[b] |
| Total sperm count (×10$^9$) | 93.515[a] | 104.000[a] |
| Period 2 (7–16 weeks) | | |
| Volume (ml) | 150.395[a] | 178.775[b] |
| Sperm density (×10$^9$/ml) | 0.650[a] | 0.568[b] |
| Total sperm count (×10$^9$) | 95.294[a] | 96.404[a] |

[a,b]means not sharing superscripts differ significantly ($P < 0.05$)

| Reproduction | | | |
|---|---:|---:|---:|
|  | Control | NOVASTA | P-value |
| Farrowing rate, % | 71 | 76 | 0.11 |
| Born alive, pigs/sow | 9.2 | 9.7 | 0.009 |
| Born dead, pigs/sow | 0.8 | 0.9 | 0.24 |
| Born in total, pigs/sow | 10.0 | 10.6 | 0.003 |

From the above results it is evident that

NOVASTA significantly ($P<0.05$) increased semen volume and in boars during a 16 week period Total sperm count increased by on average 6.2 per cent ($P>0.05$) in boars fed NOVASTA Feeding NOVASTA to AI boars significantly ($P<0.05$) increased the number of piglets born alive by 5.4 per cent in sows mated with their semen The response to NOVASTA in terms of semen volume was much more dramatic in the first 6-weeks of the experiment than in the subsequent 10-week period. The number of sperms produced decreased for both treatment groups during the latter period. However, boars fed NOVASTA produced higher number of sperms in both periods. This was not statistically significant.

The matings resulted in 378 farrowings out of 513 matings of sows mated with boars fed NOVASTA and 359 farrowings out of 523 matings of sows mated with boars of the control group.

What is claimed is:

1. A method of increasing the volume, the total sperm count and the reproductive performance of semen from human or animal males, comprising administration of a quality improving dosage of a human or a veterinarian preparation wherein astaxanthin is an active ingredient in said preparation, to said males.

2. A method according to claim 1, wherein the effective dosage of the preparation contains 0.01 to 1 mg astaxanthin per kg body weight per day.

3. A method according to claim 1, wherein the astaxanthin is in a form esterified with fatty acids.

4. A method according to claim 3, wherein the esterified astaxanthin is in the form of algal meal produced by culturing of the alga Haematococcus sp.

5. A method according to claim 3, wherein the effective dosage of the preparation contains 0.01 to 1 mg astaxanthin per kg body weight per day.

6. A method according to claim 4, wherein the effective dosage of the preparation contains 0.01 to 1 mg astaxanthin per kg body weight per day.

\* \* \* \* \*